United States Patent [19]

Alison

[11] 4,202,324
[45] May 13, 1980

[54] EQUINE VAGINAL SPECULUM

[76] Inventor: W. Evans Alison, Rte. 1, Brownsboro, Ala. 35741

[21] Appl. No.: 891,524

[22] Filed: Mar. 30, 1978

[51] Int. Cl.² ............................................. A61B 17/02
[52] U.S. Cl. ...................................... 128/20; 128/341
[58] Field of Search ................. 128/3, 4, 20, 17, 19, 128/341, 361, 303 R

[56] References Cited

U.S. PATENT DOCUMENTS

| | | | |
|---|---|---|---|
| 516,842 | 3/1894 | Scheerer | 128/20 |
| 1,796,072 | 3/1931 | Baer | 128/3 |
| 1,894,725 | 1/1933 | Bacon | 128/3 |
| 2,083,573 | 6/1937 | Morgan | 128/3 |
| 2,300,040 | 10/1942 | Betts | 128/3 |
| 2,579,849 | 12/1951 | Newman | 128/3 |
| 2,666,428 | 1/1954 | Glenner | 128/20 |
| 3,037,505 | 6/1962 | Walden et al. | 128/3 |
| 3,709,215 | 1/1973 | Richmond | 128/20 |

FOREIGN PATENT DOCUMENTS

| | | | |
|---|---|---|---|
| 15943 | 4/1904 | Austria | 128/20 |
| 83488 | 4/1921 | Austria | 128/20 |
| 736181 | 11/1932 | France | 128/361 |

OTHER PUBLICATIONS

Codman, General Surgical Instruments-Catalog-2/19-75-(Published), p. 144-Randolph, Mass. 02368.

Primary Examiner—Robert W. Michell
Assistant Examiner—Arthur S. Rose
Attorney, Agent, or Firm—C. A. Phillips

[57] ABSTRACT

An elongated speculum blade for insertion horizontally into the vagina of a standing animal. From an end of the blade a balancing weight extends adjustably vertically downward and adjustably horizontally under the blade, enabling the speculum to be self-supporting. With this blade in place, a second blade may be inserted and freely moved to observe particular regions in the vagina.

5 Claims, 5 Drawing Figures

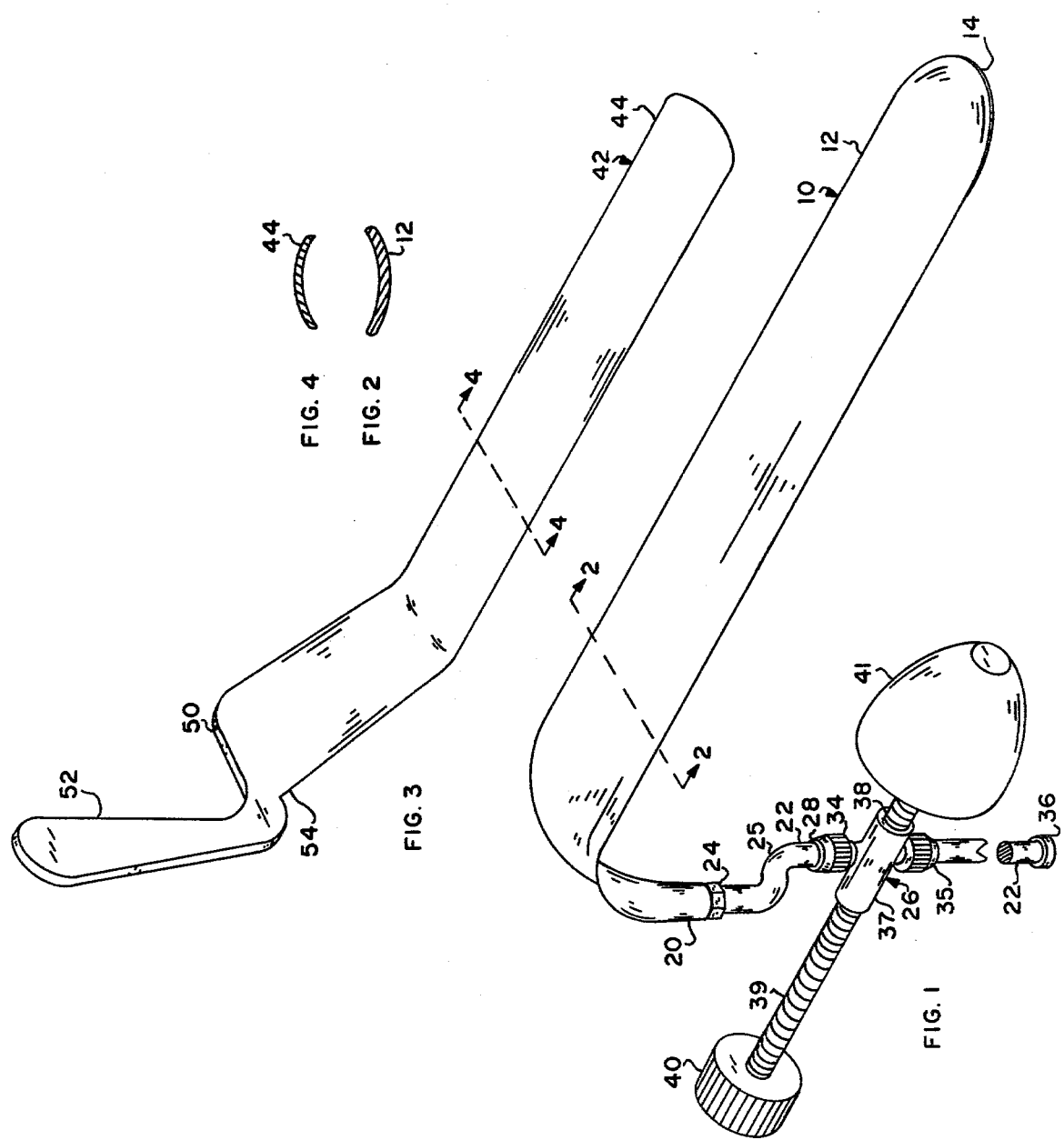

EQUINE VAGINAL SPECULUM

BACKGROUND OF THE INVENTION

1. Field of the Invention

This invention relates to devices and methods for using devices for viewing and gaining access to body cavities, particularly the vagina of a four-legged, standing animal.

2. General Description of the Prior Art

Vaginal inspections are generally made while using some form of vaginal wall spreading instrument. The most common form in use today is referred to as a speculum and employs a pair of pivotally connected blades similar in operation to scissors blades, whereby the blades may be adjustably spread by an adjustable separation of blade handles. A difficulty with this device is that there is no direct view or access into a cavity being inspected between the blades because of the necessary pivot, and this makes inspection and treatment procedures more difficult.

Another form of speculum, described in a prior patent, suggests the employment of four blades which operate similar to the iris of a camera, and which would be self-supporting. It appears that this would have merit, but it also appears likely that four blades would excessively obscure portions of the cavity being inspected.

It is an object of this invention to overcome the apparent difficulties with previously known speculums and to provide one which offers less obstruction in viewing and treatment, especially surgery treatment, of a body cavity.

SUMMARY OF THE INVENTION

In accordance with this invention, an elongated dished blade is provided for horizontal insertion into the vagina of a standing animal. A handle extends vertically downward (as used) from an end of the blade, and to it is attached a weight holder which extends horizontally under the blade. A weight is adjustably held by the weight holder to provide a balanced holding of the blade in a discrete position in the vagina. Alternately, the weight holder and weight may be a single structure. As a further means for opening and spreading the walls of a vagina, a second blade would be employed which includes a handle by which an operator may move the second blade infinitely within the vagina. Thus, only a single hand is necessary for operation of the blades, and thus the other hand is free for treatment procedures.

BRIEF DESCRIPTION OF THE DRAWINGS

FIG. 1 is a pictorial view of a blade assembly with an attached weight.

FIG. 2 is a sectional view along lines 2—2 of FIG. 1.

FIG. 3 is a pictorial view of a second and additional blade assembly.

FIG. 4 is a sectional view along lines 4—4 of FIG. 3.

DETAILED DESCRIPTION OF THE DRAWINGS

Figure 5:
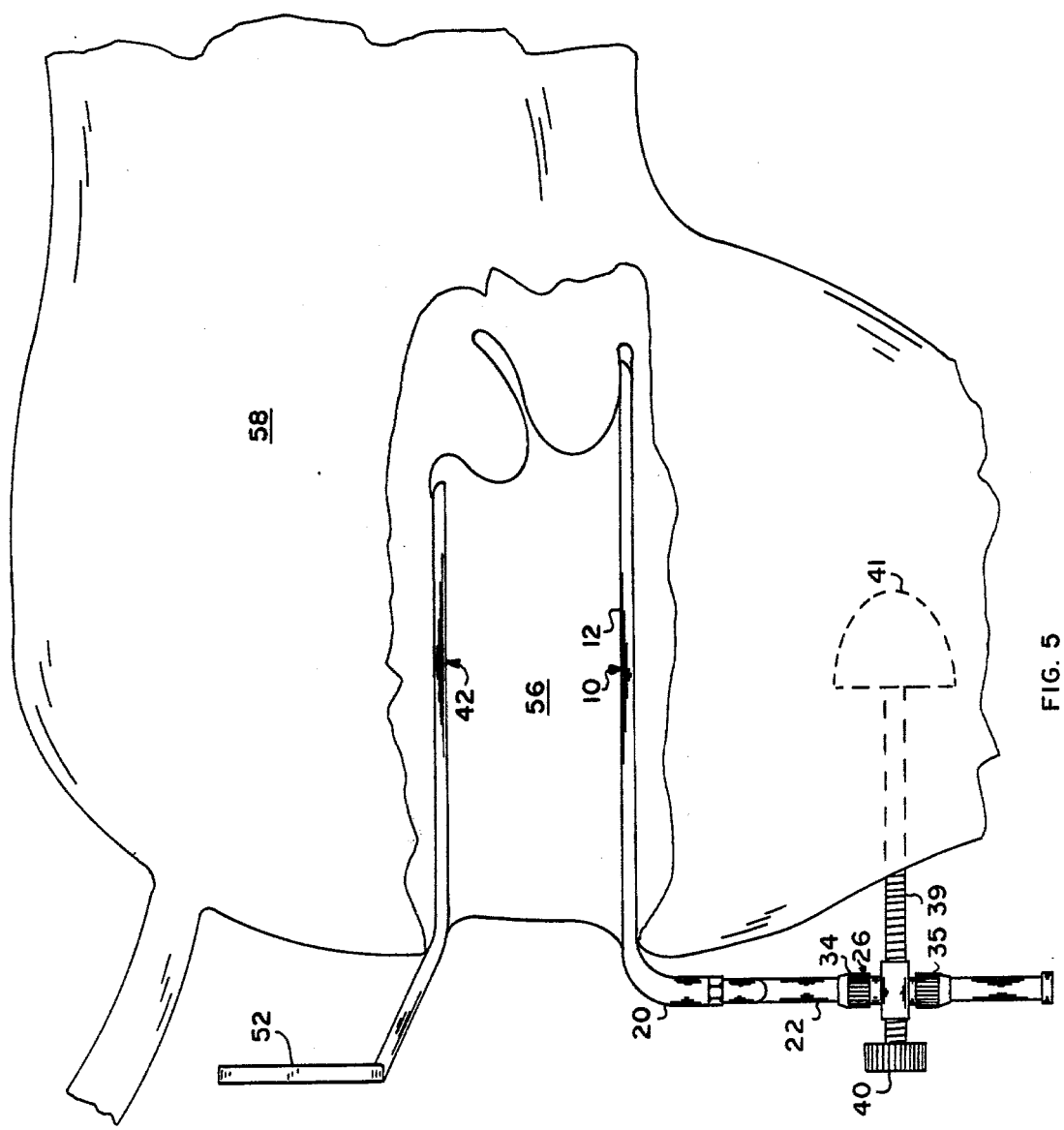
FIG. 5 is a partially diagrammatic, partially schematic cutaway elevational view of an animal with the instruments depicted in FIGS. 1-4 in operating position.

Referring to FIG. 1, blade assembly 10 includes an elongated, slightly dished blade 12 as seen in the cross sectional view in FIG. 2. Blade 12 is illustrated with its elongated portion extending horizontally as it would be used with a standing animal, and end 14 is curved to facilitate insertion in an animal. An opposite end portion of blade 12 curves downward to form a handle region 20 which generally extends normal to the longitudinal dimension of blade 12. Rod 22 is threaded into handle 20, being rigidly held by lock nut 24. Rod 22 extends downward and below offset bend 25 and supports adjustment assembly 26 which has an opening 28 through which rod 22 extends. Adjustment assembly 26 is locked into a vertical position along rod 22 by chucks 34 and 35 which clamp adjustment assembly 26 at any position along rod 22, being limited in downward travel by stop 36. Adjustment assembly 26 has in annular region 37 a horizontally positioned threaded opening 38 extending along a line of direction generally parallel with the line of direction of dished blade 12 and supporting threaded rod 39. Threaded rod 39 has a rigidly attached handle 40 on one end and supports a rigidly attached weight 41 on the other end. Rod 39 extends generally parallel with and beneath blade 12, enabling weight 41 to achieve infinite positions along blade 12 as rod 39 is rotated by handle 40.

Referring to FIGS. 3 and 4, additional blade assembly 42 is shown poised over blade assembly 10, demonstrating how the two blade assemblies would be typically used together. Blade assembly 42 has an elongated blade 44 which is dished and slightly shorter and narrower than blade 12. The left end region of blade 44 extends slightly upward from the general plane of blade 44 to terminate in end 50. An integral handle 52 extends upward from side region 54 of end 50, and thus does not interfere with blade assembly 10.

FIG. 5 illustrates more specifically the use of the invention, and as shown, blade 12 of blade assembly 10 would be inserted in the vagina 56 of an animal 58 (typically a horse or cow). Next, adjustment assembly 26 would be moved vertically on rod 22 until weight 41 hangs freely between the animal's legs, whereupon chucks 34 and 35 would be tightened. Next, weight 41 would be horizontally adjusted by rotation of threaded rod 39 in adjustment assembly 26 until blade 12 is horizontally balanced in a stable position. At this point, the operator may let go of blade assembly 10 and insert blade assembly 42 by holding, in one hand, handle 52. Blade assembly 42 can then be freely moved with one hand to facilitate observation and by the other hand effect any desired treatment.

Having thus described my invention, what is claimed is:

1. An instrument for vaginal inspection of a standing animal comprising:

a generally straight, elongated blade having a curve-shaped cross section normal to the length of the blade;

an elongated generally straight arm extending generally at a right angle from an end of said blade;

an elongated generally straight shaft extending from said arm generally parallel to and spaced from and directly under said blade;

a weight;

means for supporting said weight on said shaft, means for adjusting the distance between said weight and said arm along the line defined by the axis of said shaft, the combination of said shaft and weight being configured with an overall width approximately no greater than the width of said blade, whereby the shaft and weight may readily extend between the legs of a standing animal; and the combination of said blade, arm, and weight being freely suspendable from the vagina of a standing animal;

whereby, when said elongated blade is inserted vaginally and generally horizontally in a standing animal, said weight member will freely cause a generally downward force to be applied to the underside of the blade at points of engagement of the blade along the length of the blade with the animal.

2. An instrument as set forth in claim 1 wherein said arm comprises means for adjustably attaching said shaft along said arm, whereby the separation between weight member and blade is adjustable.

3. An instrument as set forth in claim 1 wherein said arm comprises means for adjustably attaching said shaft along said arm, whereby the separation between weight member and blade is adjustable.

4. The method of vaginal inspection of a standing animal comprising:

inserting horizontally into the vagina of an animal a generally straight, elongated blade having a curve-shaped cross section normal to the longitudinal dimension of the blade, and having a concave side of the blade facing upward, and said blade further including:

an elongated generally straight arm extending generally at right angles from an end region of said blade which is an outer end region of said blade as said instrument is inserted in said animal, an elongated generally straight shaft extending from said arm generally parallel to and spaced from and directly under said blade, said shaft being adjustable along the length of said arm, a weight member approximately no wider than said blade, and means for adjustably positioning said weight member on said shaft an adjustable distance from said arm directly under said blade and between the legs of an animal; and adjusting the vertical attachment position of the weight member on said arm and the horizontal position of said weight member, said weight being positioned between the legs of the animal, and said elongated blade being stably positioned in, but free of other instruments in, the vagina of a standing animal.

5. A method as set forth in claim 4 followed by the insertion of a second, generally straight, elongated blade, and said second elongated blade having a handle, whereby said second elongated blade may be adjustably positioned within the vagina for inspection and treatment with one hand, and the other hand being left free for treatment procedures.

* * * * *